United States Patent
Kim et al.

(10) Patent No.: US 7,719,760 B2
(45) Date of Patent: May 18, 2010

(54) OPTICAL MICROSCOPE SYSTEM FOR DETECTING NANOWIRES USING POLARIZER AND FAST FOURIER TRANSFORM

(75) Inventors: Eun Kyoung Kim, Daejeon (KR); Seung Eon Moon, Daejeon (KR); Hong Yeol Lee, Chungcheongbuk-do (KR); Jong Hyurk Park, Daegu (KR); Kang Ho Park, Daejeon (KR); Jong Dae Kim, Daejeon (KR); Gyu Tae Kim, Seoul (KR); Do Young Jang, Seoul (KR); Eung Seook Park, Seoul (KR); Hyun Jin Ji, Seoul (KR)

(73) Assignee: Electronics and Telecommunications Research Institute, Seoul (KR)

( * ) Notice: Subject to any disclaimer, the term of this patent is extended or adjusted under 35 U.S.C. 154(b) by 200 days.

(21) Appl. No.: 11/940,379

(22) Filed: Nov. 15, 2007

(65) Prior Publication Data

US 2009/0195869 A1    Aug. 6, 2009

(30) Foreign Application Priority Data

Dec. 5, 2006    (KR) ...................... 10-2006-0122347
Jun. 22, 2007   (KR) ...................... 10-2007-0061460

(51) Int. Cl.
G02B 21/06    (2006.01)
(52) U.S. Cl. ...................................... 359/386; 977/881
(58) Field of Classification Search ........................ None
See application file for complete search history.

(56) References Cited

U.S. PATENT DOCUMENTS 5,914,782 A *   6/1999  Sugiyama .................... 356/491
2003/0189202 A1  10/2003  Li et al.
2004/0136866 A1   7/2004  Pontis et al.
2005/0088663 A1 *  4/2005  De Groot et al. ............ 356/497

(Continued)

FOREIGN PATENT DOCUMENTS

JP          09-097332          4/1997

(Continued)

OTHER PUBLICATIONS

English Machine translation of JP10-104524.*

(Continued)

*Primary Examiner*—Lee Fineman
(74) *Attorney, Agent, or Firm*—Rabin & Berdo, P.C.

(57) ABSTRACT

Provided is an optical microscope system for detecting nanowires to allow for use of an existing optical microscope in fabricating an electronic device having the nanowires and including: a light source for emitting light to provide the light to a nanowire sample; a rotational polarizer provided on a path of the light emitted from the light source for polarizing the light; an optical microscope for detecting a nanowire image using light that is polarized by the rotational polarizer and incident on the nanowire sample; a CCD camera provided in a region of the optical microscope for photographing and storing the nanowire image detected by the optical microscope; and a data processor for performing Fast Fourier Transform (FFT) on the nanowire image stored in the CCD camera. Intensity of reflected light varies, due to optical anisotropy of the nanowires, along a polarizing orientation of light incident on the nanowires.

7 Claims, 3 Drawing Sheets

U.S. PATENT DOCUMENTS

2006/0012872 A1   1/2006   Hayashi et al.

FOREIGN PATENT DOCUMENTS

| JP | 10-104524 | 4/1998 |
| JP | 10-268200 | 10/1998 |
| KR | 1020000047818 A | 7/2000 |

OTHER PUBLICATIONS

Dong Jin Oh, et al., "Simple Microscale Selective Patterning on a Single Nanowire by Using an Optical Microscope" Optical Microlithography XVIII. Edited by Bruce W. Smith, Proceedings of the SPIE, vol. 5754, pp. 1500-1507 (2005).

* cited by examiner

θ = 90 °C ained in the art. In the drawings, the thickness of layers and regions are exaggerated for clarity. Like reference numerals in the drawings denote like elements, and thus their description will be omitted.

OPTICAL MICROSCOPE SYSTEM FOR DETECTING NANOWIRES USING POLARIZER AND FAST FOURIER TRANSFORM

CROSS-REFERENCE TO RELATED APPLICATION

This application claims priority to and the benefit of Korean Patent Application No. 2006-122347, filed Dec. 5, 2006, and No. 2007-61460, filed Jun. 22, 2007, the disclosure of which is incorporated herein by reference in its entirety.

BACKGROUND

1. Field of the Invention

The present invention relates to an optical microscope system for detecting nanowires, and more particularly, to an optical microscope system for detecting nanowires by means of a conventional optical microscope to facilitate alignment of a nanowire sample with a pattern.

The present invention has been produced from the work supported by the IT R&D program of MIC (Ministry of Information and Communication)/IITA (Institute for Information Technology Advancement) [2006-S-006-01, Components/Module technology for Ubiquitous Terminals] in Korea.

2. Discussion of Related Art

Photolithography processes are essential for fabricating electronic devices with nanowires. Especially, in patterning a structure for fabricating an electronic device, a basic requirement is a technique for obtaining a sampling image to align a sample with a pattern during photolithography.

A diameter of a nanowire used in fabricating a nanowire electronic device usually ranges from several nanometers to several tens of nanometers. A length of the nanowire generally ranges from several tens of nanometers to several micrometers, or several micrometers to several tens of micrometers. In fabricating an electronic device by means of nanowires that are relatively thick, that is, in the range of several tens of nanometers in diameter and in the range of several micrometers in length, as it is easy to obtain a sampling image by a general optical microscope, conventional semiconductor manufacturing equipment is available for aligning a sample to a pattern.

But, if nanowires used for fabricating an electronic device are relatively fine, that is, in the range of 0~20 nanometers in diameter (specifically, less than 10 nm or 10~20 nm), it is not easy to obtain a nanowire image by a conventional optical microscope. Furthermore, even in the case of using single-wall carbon nanotubes with a thickness of several nanometers for fabricating an electronic device, it is also difficult to obtain a nanowire image by a conventional optical microscope.

For the purpose of solving the aforementioned problems, a high-resolution microscope, such as an atomic force microscope (AFM) or scanning electron microscope (SEM), is employed in fabricating an electronic device with nanowires or carbon nanotubes that are finer in diameter, because it is much better resolution than an optical microscope and therefore advantageous in obtaining a distinct sampling image necessary for the alignment process.

However, such a high-resolution microscope is relatively expensive and requires more time to obtain a sampling image than the optical microscope, and therefore it is disadvantageous to commercial use. In addition, it is not easy to commercially fabricate a nanowire device on a large scale.

SUMMARY OF THE INVENTION

The present invention is directed to an optical microscope system for detecting nanowires that is capable of obtaining an image of fine nanowires or carbon nanotubes by means of an optical microscope used in a normal semiconductor fabrication process.

The present invention is also directed to an optical microscope system for detecting nanowires that is capable of aligning a nanowire sample to a pattern in a shorter time and a lower cost.

One aspect of the present invention provides an optical microscope system for detecting nanowires, comprising: a light source for emitting light to provide the light to a nanowire sample; a rotational polarizer provided on a path of the light emitted from the light source for polarizing the light; an optical microscope for detecting a nanowire image using light that is polarized by the rotational polarizer and incident on the nanowire sample; a CCD camera provided in a region of the optical microscope for photographing and storing the nanowire image detected by the optical microscope; and a data processor for performing Fast Fourier Transform (FFT) on the nanowire image stored in the CCD camera.

The optical microscope system may further comprise a polarizer controller electrically coupled to the rotational polarizer for rotating the rotational polarizer. The rotational polarizer may use optical anisotropy of the nanowires and modulate a polarizing orientation of the light incident on the nanowire sample. The polarizer controller may control to rotate the rotational polarizer at a frequency ($f_0$) of 0.1 Hz through 1 Hz. The rotation of the rotational polarizer may modulate a polarizing axis of the light incident on the nanowire sample into $2f_0$. When the light emitted from the light source is changed into light at a uniform frequency by the polarizer controller and the light incident on the nanowire sample is modulated into a specific frequency, image data of the nanowires may be processed by the FFT after storing the modulated frequency information in a pixel arrangement over time.

BRIEF DESCRIPTION OF THE DRAWINGS

The above and other features and advantages of the present invention will become more apparent to those of ordinary skill in the art by describing in detail preferred embodiments thereof with reference to the attached drawings in which:

FIG. 2 schematically shows three-dimensional nanowire image data taken by a CCD camera and image data obtained from the three-dimensional nanowire image data by Fast Fourier Transform.

DETAILED DESCRIPTION OF EXEMPLARY EMBODIMENTS

Hereinafter, exemplary embodiments of the present invention will be described in detail. However, the present invention is not limited to the embodiments disclosed below, but can be implemented in various forms. Therefore, the following embodiments are described in order for this disclosure to be complete and enabling to those of ordinary skill in the art.

Figure 1:
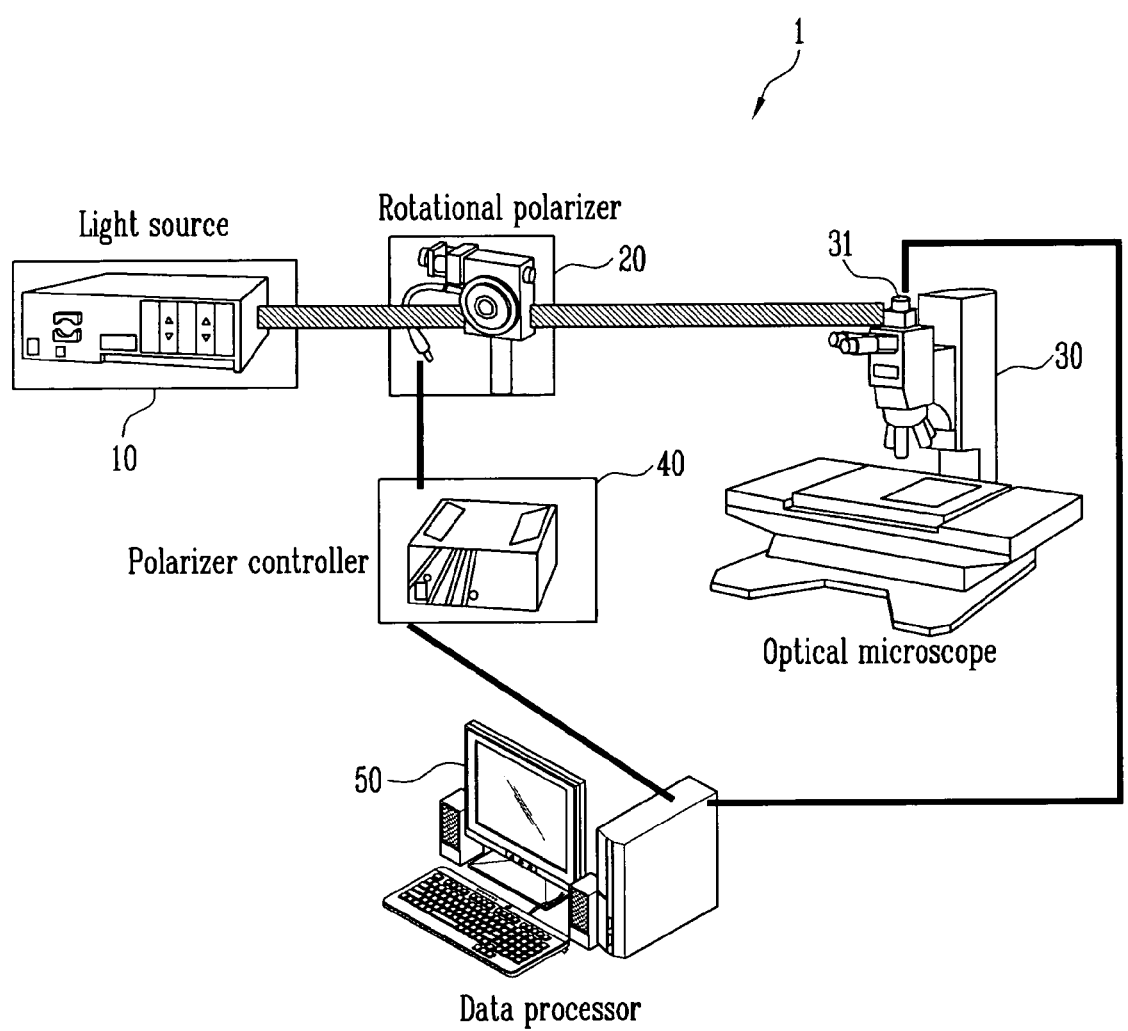
FIG. 1 shows an optical microscope system for detecting nanowires in accordance with the present invention.

FIG. 1 shows an optical microscope system for detecting nanowires in accordance with the present invention. The nanowire-detecting optical microscope system 1 comprises a light source 10 for emitting light, an optical microscope 30 including a charge-coupled device (CCD) camera 31 for photographing an image of light reflected from a nanowire sample (not shown), and a rotational polarizer 20 interposed between the light source 10 and the optical microscope 30. Light emitted from the light source 10 arrives at the nanowire sample and then the CCD camera 31 captures an optical image (i.e., optical data) from the nanowire sample. The optical data obtained by the CCD camera 31 is processed by Fast Fourier Transform (FFT).

Referring to FIG. 1, the nanowire-detecting optical microscope system 1 according to the present invention comprises the light source 10 for emitting light, the rotational polarizer 20 for polarizing the light of the light source 10 in a specific direction, a polarizer controller 40 electrically connected to the rotational polarizer 20 for controlling the rotation of the polarizer 20, the optical microscope 30 for detecting an optical nanowire image from the light that is reflected from the nanowire sample after transmitting through the rotational polarizer 20, the CCD camera 31 installed in a region of the optical microscope 30 for photographing the optical nanowire image and storing data of the optical nanowire image, and a data processor 50 for performing the FFT on the nanowire image data obtained by the CCD camera 31.

In more detail, the light source 10 provides white light to the nanowire sample. The rotational polarizer 20, as a device for obtaining polarization from an effect that transmission light polarized by orientation varies in color in an optical isomer (or enantiomer), polarizes the white light of the light source 10. The white light transmitting through the rotational polarizer 20 is polarized in a specific direction. When the polarized light is incident on the nanowires, most nanowires exhibit optical anisotropy that a pattern of light emission varies with an angle between an orientation of the nanowires and a polarizing axis. The polarized light is emitted at maximum when the nanowire orientation is aligned to the polarizing axis and the angle thereof becomes 0°. Otherwise, when the angle between the nanowire orientation and the polarizing axis is 90°, the polarized light is emitted at minimum. Using such optical anisotropy of the nanowires, it is possible to implement the high-resolution optical microscope system.

In this embodiment, the polarizer controller 40 is used for controlling the rotational polarizer 20. The polarizer controller 40 is disposed between the light source 10 and the optical microscope 30, controlling the rotational polarizer 20 to rotate with a frequency $f_0$ in the range of 0.1~1 Hz. The optical microscope 30 is generally capable of detecting nanowires of the nanowire sample by means of the white light provided from the light source 30. The CCD camera 31 of the optical microscope 30 takes an image from the polarized light that is reflected from the nanowire sample after transmitting through the rotational polarizer 20.

While in this embodiment, the CCD camera 31 is located on the ocular of the optical microscope 30, the CCD camera 31 may be located at the bottom of the ocular or another region of the optical microscope 30 to be operable externally by a remote control. The image data of the nanowire sample, which is obtained through the CCD camera 31, is stored in a regular period. The CCD camera 31 is remotely controlled to store the image data in the data processor 50 that processes the image data. The data processor 50 removes noise from the image data, which is taken by the CCD camera 31, by way of the FFT, to obtain an image of fine nanowires whose diameters range in 10~20 nanometers or carbon nanotubes whose diameters range in several nanometers.

According to the optical microscope system 1, as the polarizer controller 40 controls the rotational polarizer 20 to rotate with the specific frequency $f_0$ of 0.1~1 Hz, the polarizing axis of the polarized light incident on the nanowire sample rotates at a frequency of $2f_0$. Accordingly, the angle between the nanowire axis and the polarizing axis changes to the frequency of $2f_0$, and the intensity of light reflected from the nanowires is also modulated into the frequency of $2f_0$. Otherwise, since a peripheral sample around the nanowires generally has no optical anisotropy or small optical anisotropy, a component modulated into the frequency of $2f_0$ of the intensity of light reflected from the peripheral sample is relatively less than that of the nanowires. As a result, by selectively obtaining a signal modulated into the specific frequency $2f_0$ corresponding to the nanowires, signals in the peripheral region without the nanowires are removed, such that a distinct nanowire image is obtained. The method of obtaining a nanowire image uses a principle of a lock-in amplifier that only a desired specific frequency signal is extracted from a noisy environment.

The optical microscope 30 employed in the optical microscope system 1 has a magnification of 1000 through 2500 times. The CCD camera 31 stores images of the nanowire samples as motion pictures of 30~40 frames per second for 2~20 seconds while the polarizer 20 is rotating. In this case, it is efficient for the CCD camera 31 to have 640×480 or more pixels. Image data taken by the CCD camera 31, which is stored by frame, can be represented in a two-dimensional arrangement of $n_0$ (row)×$m_0$(column) pixels. Each pixel contains information on intensity (I) of the light reflected from the nanowire sample. Thus, intensity information of the (n, m)-th pixel may be represented by I(n, m). In the meantime, since each frame is stored at uniform intervals (2~20 seconds) as previously mentioned, the light intensity information I is represented in a three-dimensional arrangement shown in FIG. 2 in consideration of the time axis.

Figure 2:
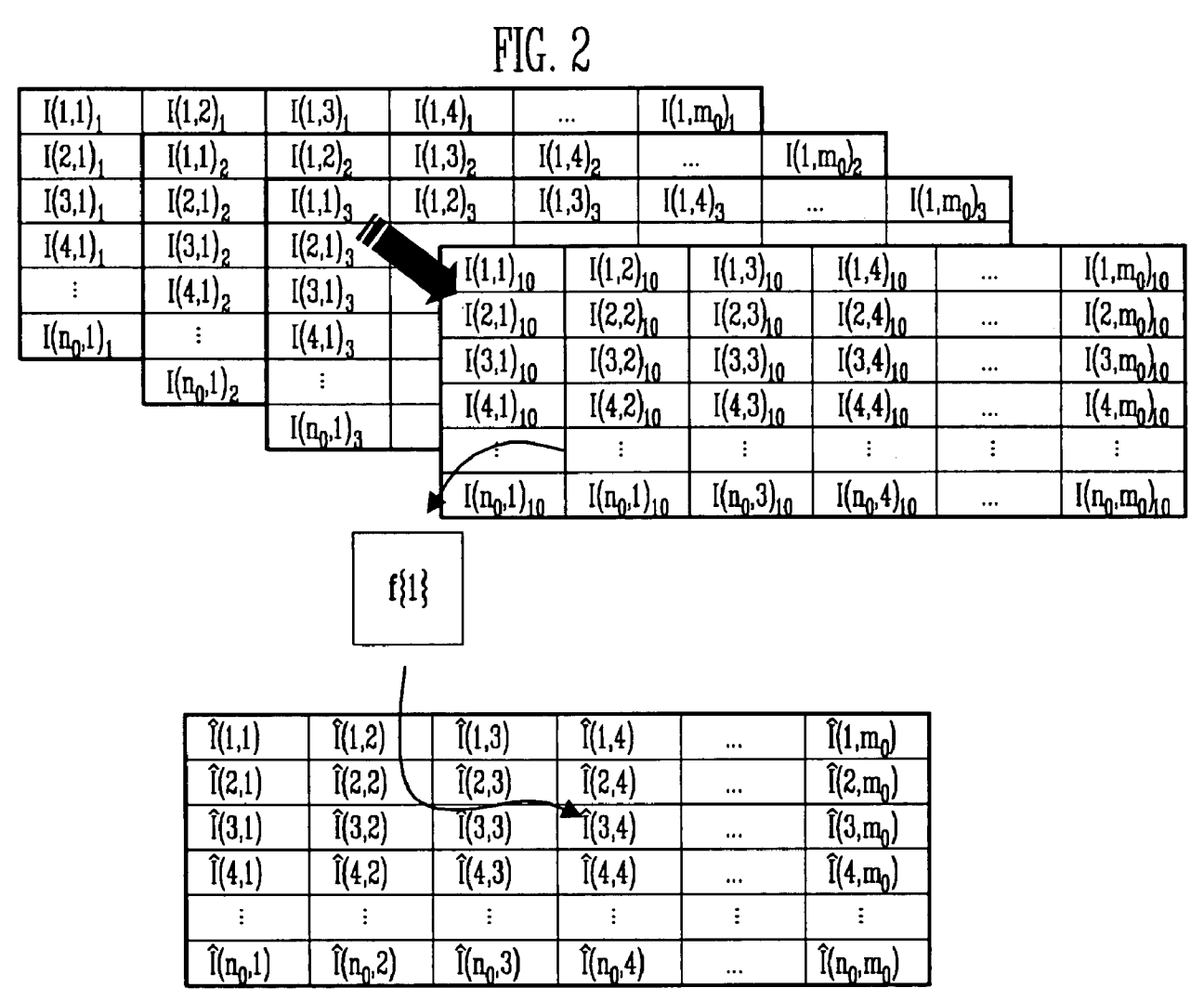

FIG. 2 schematically shows three-dimensional nanowire image data taken by the CCD camera and image data obtained from the three-dimensional nanowire image data by the FFT. Referring to FIG. 2, on the time axis, the CCD image frames are stored in the total number of $I_0$ that is equal to (the number of CCD image frames per second)×(motion picture storage time). If the light intensity information of the (n,m) pixel of l'th frame can be represented by $I(n,m)_l$, the light intensity information of the (n,m) pixel is arranged in the sequence of $I(n.m)_1, I(n.m)_2, I(n.m)_3, \ldots,$ and $I(n.m)_{10}$ on the time axis. As each pixel has the data in a number of 10, it is possible to obtain frequency information to the light intensity information. In particular, if a new image is obtained from selecting a Fourier coefficient in correspondence with the frequency $2f_0$, it is possible to abstract an image of the nanowires modulated into the frequency $2f_0$. Since the time based data of pixel, $I(n.m)_1, I(n.m)_2, I(n.m)_3, \ldots,$ and $I(n.m)_{10}$, is discrete data, it is possible to obtain the Fourier coefficient through the FFT in correspondence with the frequency $2f_0$. The procedure of obtaining the Fourier coefficient from the 10 data (e.g., 30~40 frames×2~20 seconds) per pixel is necessary to conduct the calculation 102 times in total, and these calculation cycles must be executed to $n_0 \times m_0$ (e.g., 640480). However, the FFT is helpful to reduce the number of calculation cycles, and enhance the image processing speed. FIG. 2 shows a schematic model resulting in new image pixels by obtaining complex-number Fourier coefficients $(2f_0)n,m$ from the temporal pixel data $I(n,m)_1$ by way of the FFT in correspondence with the frequency $2f_0$. The nanowire image is obtained from absolute values of the complex-number Fourier coefficients.

In the meantime, phase information of the Fourier coefficient has information about the axial orientation of the nanowires. Light reflected from the nanowires having different axial orientation is modulated at uniform time intervals, resulting in phase difference between the Fourier coefficients. Thus, using the fact that a specific phase value of the Fourier coefficients means an angle of the axial orientation of the nanowires corresponding thereto, it is possible to selectively show the nanowires aligned to a specific orientation on an image.

Figure 3A:
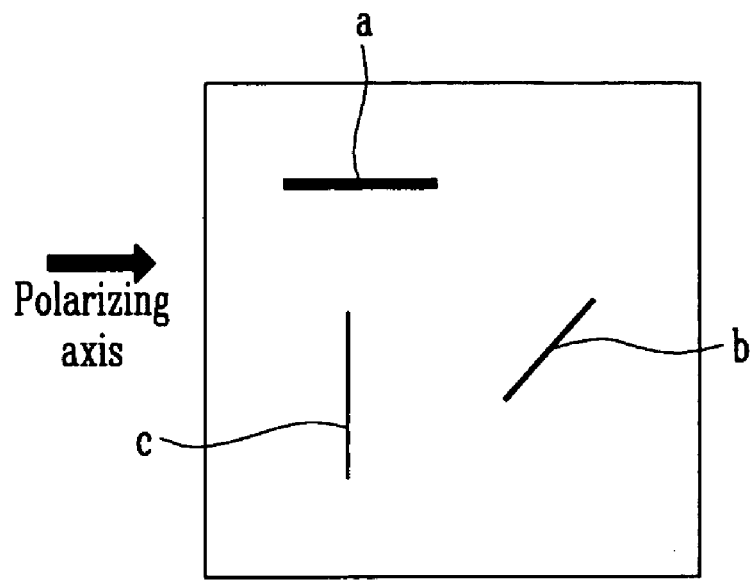
FIGS. 3A and 3B are image diagrams showing cases when an angle between the polarizer and a reference axis of the nanowire sample is 0° and 90°, respectively, representing image data obtainable from the nanowire sample by means of the optical microscope system shown in FIG. 1.
Figure 3B:
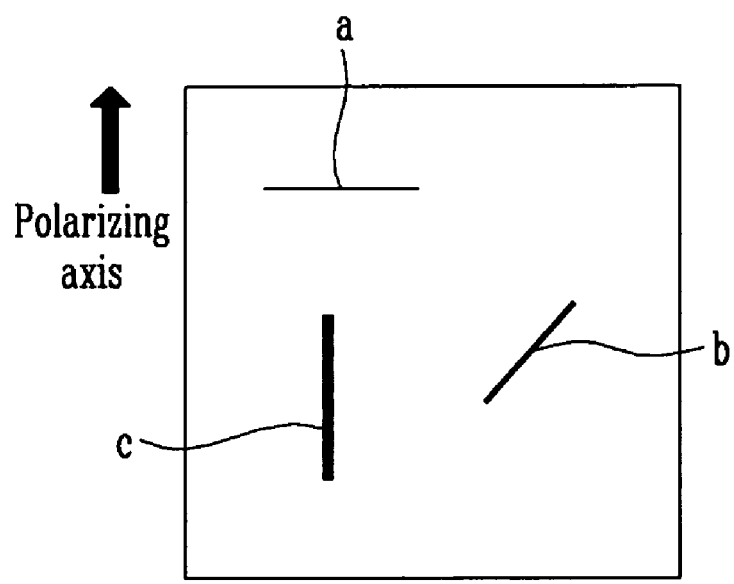

FIGS. 3A and 3B are image diagrams showing cases when an angle between the polarizer and a reference axis of the nanowire sample is 0° and 90°, respectively, representing image data obtainable from the nanowire sample by means of the optical microscope system shown in FIG. 1. As previously mentioned, θ indicates an angle between the polarizing axis and the nanowire used as the reference axis. FIG. 3A corresponds to the case when an angle between the polarizing axis and the nanowire reference axis is 0°, while FIG. 3B corresponds to the case when an angle between the polarizing axis and the nanowire reference axis is 90°. Generally, light transmitting through the rotational polarizer 20 is polarized to a specific orientation according to a rotation angle of the polarizer 20. If the polarizing axis is horizontal to the nanowire reference axis, i.e., an angle between the polarizing axis and the nanowire reference axis is 0°, the brightness of the nanowires horizontal to the polarizing axis is maximized while the brightness of the nanowires vertical to the polarizing axis is minimized. Otherwise, if the polarizing axis is vertical to the nanowire reference axis, i.e., an angle between the polarizing axis and the nanowire reference axis is 90°, the brightness of the nanowires parallel to the polarizing axis is maximized.

Referring to FIG. 3A, among three nanowires a, b, and c, the nanowire a parallel to the polarizing axis has the highest brightness, whereas the nanowire c has the lowest brightness. Referring to FIG. 3B, among the three nanowires a, b, and c, the nanowire a vertical to the polarizing axis has the lowest brightness, whereas the nanowire c has the highest brightness.

As described above, the present invention can reduce processing time and production cost by using an existing optical microscope in fabricating an electronic device with nanowires that are several nanometers or 10~20 nm in diameter or with carbon nanotubes that are several nanometers (0~10 nm) in thickness.

In addition, an optical microscope for an existing semiconductor device process can be utilized, resulting in excellent process linkage and electronic devices with nanowires or carbon nanotubes on a large scale.

Moreover, the nanowire image can be obtained by using the optical microscope instead of using an expensive electron microscope (or an atomic force microscope), thus contributing to activation of studies on nanowires.

While the invention has been shown and described with reference to certain exemplary embodiments thereof, it will be understood by those skilled in the art that various changes in form and detail may be made therein without departing from the spirit and scope of the invention as defined by the appended claims.

What is claimed is:

1. An optical microscope system for detecting nanowires, comprising:
    a light source for emitting light to provide the light to a nanowire sample;
    a rotational polarizer provided on a path of the light emitted from the light source for polarizing the light;
    a polarizer controller electrically coupled to the rotational polarizer for rotating the rotational polarizer at a first frequency;
    an optical microscope for detecting a nanowire image using the light that is polarized by the rotational polarizer and incident on the nanowire sample;
    a CCD camera provided in a region of the optical microscope for photographing and storing the nanowire image detected by the optical microscope; and
    a data processor for selectively extracting only pixels corresponding to the nanowire sample from the nanowire image using Fast Fourier Transform (FFT) and obtaining a new nanowire image,
    wherein when the light polarized by the rotation of the rotational polarizer is incident on the nanowire sample, intensity of light that is reflected from the nanowire sample is modulated into a second frequency due to the optical anisotropy of the nanowire sample, and the data processor selectively extracts only pixels corresponding to the second frequency from the nanowire image, and obtains a new nanowire image.

2. The optical microscope system of claim 1, wherein the polarizer controller controls to rotate the rotational polarizer at the first frequency ($f_0$) of 0.1 Hz through 1 Hz.

3. The optical microscope system of claim 2, wherein the rotation of the rotational polarizer modulates a polarizing axis of the light incident on the nanowire sample into the second frequency ($2f_0$).

4. The optical microscope system of claim 3, wherein an angle between an axis of the nanowire sample and a polarizing axis of the light incident on the nanowire sample is modulated into the second frequency ($2f_0$), so that the intensity of light reflected from the nanowire sample is modulated into the second frequency ($2f_0$).

5. The optical microscope system of claim 4, wherein the intensity of light reflected from the nanowire sample varies according to the angle between the axis of the nanowire sample and the polarizing axis of the light incident on the nanowire sample, when the angle is 0 degrees, the intensity of light reflected from the nanowire sample is maximized, and when the angle is 90 degrees, the intensity of light reflected from the nanowire sample is minimized.

6. The optical microscope system of claim 1, wherein the data processor performs Fast Fourier Transform on the nanowire image, stores the transformed results as a pixel arrangement having information on intensity and frequency of the light reflected from the nanowire sample, and selectively extracts only Fourier coefficients corresponding to the second frequency from each pixel to obtain the new nanowire image.

7. The optical microscope system of claim 1, wherein the data processor obtains information on an axis of the nanowire sample from the Fast Fourier Transform results, and selectively extracts only pixels corresponding to the nanowire sample arranged in a specific direction according to the obtained information on the axis of the nanowire sample.

* * * * *

UNITED STATES PATENT AND TRADEMARK OFFICE
CERTIFICATE OF CORRECTION

| | |
|---|---|
| PATENT NO. | : 7,719,760 B2 |
| APPLICATION NO. | : 11/940379 |
| DATED | : May 18, 2010 |
| INVENTOR(S) | : Kim et al. |

It is certified that error appears in the above-identified patent and that said Letters Patent is hereby corrected as shown below:

On the Title Page

In item (75) in the heading of the Patent, the ninth inventor name should be spelled "Eung Seok Park."

In item (73) in the heading of the Patent, the Assignee listing section should read:

Electronics And Telecommunications Research Institute, Daejeon, Republic Of Korea
  Korea University Industrial & Academic Collaboration Foundation, Seoul, Republic of Korea Signed and Sealed this
Fifteenth Day of February, 2011

David J. Kappos
*Director of the United States Patent and Trademark Office*